US00PP11396P

United States Patent [19]

Trees

[11] Patent Number: Plant 11,396

[45] Date of Patent: May 30, 2000

[54] GERANIUM PLANT NAMED 'BFP-1705'

[75] Inventor: Scott C. Trees, Nipomo, Calif.

[73] Assignee: Ball Floraplant a division of Ball Horticultural Co., West Chicago, Ill.

[21] Appl. No.: 09/112,337

[22] Filed: Jul. 9, 1998

[51] Int. Cl.[7] ..... A01H 5/00

[52] U.S. Cl. ..... Plt./325

[58] Field of Search ..... Plt./325, 327, 328, Plt./330

[56] References Cited

U.S. PATENT DOCUMENTS

P.P. 10,397 5/1998 Trees ..... Plt./328

*Primary Examiner*—Howard J. Locker
*Assistant Examiner*—Kent L. Bell
*Attorney, Agent, or Firm*—C. A. Whealy

[57] ABSTRACT

A new and distinct cultivar of Geranium plant named 'BFP-1705', characterized by its numerous semi-double salmon and light pink-colored flowers; upright and rounded growth habit; vigorous and basal branching; and dark green leaves.

1 Drawing Sheet

BACKGROUND OF THE INVENTION

The present invention relates to a new and distinct cultivar of Geranium plant, botanically known as *Pelargonium×hortorum*, and hereinafter referred to by the cultivar name BFP-1705.

The new Geranium is a product of a planned breeding program conducted by the Inventor in Arroyo Grande, Calif. The objective of the breeding program was to develop new cultivars with excellent basal branching, medium growth habit, numerous flowers and umbels, and interesting flower and foliage colors.

The new Geranium originated from a cross made by the Inventor of the proprietary *Pelargonium×hortorum* selection 7692-17 as the male, or pollen parent, with the proprietary *Pelargonium×hortorum* selection 1192 as the female, or seed parent. The cultivar BFP-1705 was discovered and selected by the Inventor as a flowering plant within the progeny of the stated cross in a controlled environment in Arroyo Grande, Calif., on Sep. 15, 1996.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'BFP-1705'. These characteristics in combination distinguish 'BFP-1705' as a new and distinct cultivar:

1. Numerous semi-double salmon and light pink-colored flowers.
2. Upright and rounded growth habit.
3. Vigorous and basal branching.
4. Dark green leaves.

The new Geranium can be compared to the cultivar, 'Americana Light Salmon' (disclosed in U.S. Plant Pat. No. 7,936). However, in side-by-side comparisons conducted by the Inventor in Arroyo Grande, Calif., plants of the new Geranium differ from plants of the cultivar 'Americana Light Salmon' in the following characteristics:

1. Plants of the new Geranium are more vigorous than plants of the cultivar 'Americana Light Salmon'.

2. Plants of the new Geranium have larger leaves with a more distinctive zonation pattern than plants of the cultivar 'Americana Light Salmon'.
3. Plants of the new Geranium have larger flower umbels than plants of the cultivar 'Americana Light Salmon'.
4. Plants of the new Geranium have more flowers per umbel than plants of the cultivar 'Americana Light Salmon'.
5. Flower color of plants of the new Geranium is more orange than flower color of plants of the cultivar 'Americana Light Salmon'.
6. Plants of the new Geranium have longer peduncles than plants of the cultivar 'Americana Light Salmon'.

A detailed comparison of plants of the cultivar BFP-1705 and the cultivar 'Americana Light Salmon' appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in a colored reproduction of this type. The photograph comprises a side perspective view of a typical plant of 'BFP-1705'. Flower and foliage colors in the photograph may appear different from the actual colors due to light reflectance.

DETAILED BOTANICAL DESCRIPTION

The cultivar BFP-1705 has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 22° C. and night temperatures about 18° C.

In the following description, color references are made to The Royal Horticultural Society Colour Chart except where general terms of ordinary dictionary significance are used.

Botanical classification: *Pelargonium×hortorum* cultivar BFP-1705.

Parentage:

*Male parent.*—Proprietary *Pelargonium×hortorum* selection 7692-17.

*Female parent.*—Proprietary *Pelargonium×hortorum* selection 1192.

Propagation:

*Type cutting.*—Terminal cuttings.

*Time to initiate roots.*—About 7 days at temperatures about 18° C.

*Time to develop roots.*—About 21 days at temperatures about 18° C.

*Rooting habit.*—Fibrous and freely branching.

Plant description:

*General appearance.*—Upright and rounded growth habit, vigorous. Appropriate for 10 and 12.5-cm containers. About nine weeks are required to produced a finished 10-cm container from a rooted cutting.

*Growth and branching habit.*—Basally branching with about two lateral branches at the base.

*Plant height, base of plant to top of leaf plane.*—About 26.8 cm.

*Plant width.*—About 20.6 cm.

*Lateral branches.*—Length: About 11 cm. Internode length: About 1.5 cm. Color: 143B/144A.

*Foliage description.*—Leaves simple, generally symmetrical, abundant, opposite. Quantity of leaves per lateral branch: About 12. Length: About 9.5 cm. Width: About 10.4 cm. Shape: Reniform with rounded apex, cordate base, crenate and undulating margin. Texture: Downy, both surfaces pubescent. Color: Fully expanded foliage, upper surface: Slightly lighter than 147A at base, 147A towards margin. Fully expanded foliage, lower surface: 137C. Venation, upper and lower surfaces: 137C. Petiole: Length: About 5.5 cm. Diameter: About 2.4 mm. Color: Between 143B and 144A.

Flower description:

*Flower type and habit.*—Salmon and light pink-colored flowers. Very freely and continuously flowering. Flowers arranged in spherical umbels arising from apical leaf axils. Umbels displayed above or beyond the foliage. Usually about four umbels per plant. Flowers semi-double, round, slightly cupped. Umbels persistent.

*Flowering season.*—Year-round under greenhouse conditions. In the garden, flowering is continuous from spring through summer.

*Umbels.*—Number of flowers per umbel: About 52. Diameter: About 11.7 cm. Height: About 9 cm.

*Flowers.*—Diameter: About 4.6 cm. Depth (height): About 1.5 cm.

*Flower buds.*—Length: About 1.3 cm. Diameter: About 8 mm. Shape: Elliptic.

*Petals.*—Quantity: About 6 petals and about 4 petaloids, overlapping. Length: About 2.5 cm. Width: About 2.7 cm. Shape: Obovate with rounded apex and entire margin. Texture: Smooth, dull. Color: Fully opened, upper surface: 49C from base to center; center, 47D; margin, 42B. Fully opened, lower surface: 42C with 49C at base. Petaloids: Irregular in shape with very narrow base; about 1.3 cm in length and about 3 mm in width; towards margin, 42B, and base, 49C, in color.

*Peduncle* (*umbel stem*).—Length: About 18 cm. Strength: Strong. Angle: Mostly erect. Texture: Pubescent. Color: 144A.

*Pedicel* (*individual flower stem*).—Length: About 2.7 cm. Texture: Pubescent. Color: Light green, 144B with slight overtones of 182A.

*Reproductive organs.*—Androecium: Anther size: About 2 mm. Amount of pollen: Moderate. Pollen color: 31A. Gynoecium: Ovary color: Green.

Disease resistance: Under commercial conditions, resistance to pathogens has not been observed.

Seed development: Seed production has not been observed.

CHART A

| CHARACTERISTIC | 'BFP—1705' | 'AMERICANA LIGHT SALMON' |
|---|---|---|
| PLANT HEIGHT | About 26.8 cm | About 24 cm |
| PLANT WIDTH | About 20.6 cm | About 19 cm |
| LATERAL BRANCH LENGTH | About 11 cm | About 10 cm |
| INTERNODE LENGTH | About 1.5 cm | About 2.5 cm |
| LEAF LENGTH | About 9.5 cm | About 4 cm |
| LEAF WIDTH | About 10.4 cm | About 6.5 |
| LBAF TEXTURE | Downy | Leathery |
| LEAF ZONATION PATTERN | Distinct | Slight |
| WIDTH OF ZONE | About 3.5 cm | About 1.5 cm |
| UMBEL DIAMETER | About 11.7 cm | About 10.8 cm |
| UMBEL HEIGHT | About 9 cm | About 6.2 cm |
| QUANTITY OF FLOWERS PER UMBEL | About 52 | About 33 |
| PETAL COLOR, FULLY OPENED, UPPER SURFACE | 49C from base to center; center, 47D; margin, 42B | 50D at margin fading to 50C at base with veins of 50B |
| PETAL COLOR, FULLY OPENED, LOWER SURFACE | 42C with base of 49C | 56D with veins of 49C |
| PEDUNCLE LENGTH | About 18 cm | About 11 cm |

It is claimed:

1. A new and distinct cultivar of Geranium plant named 'BFP-1705', as illustrated and described.

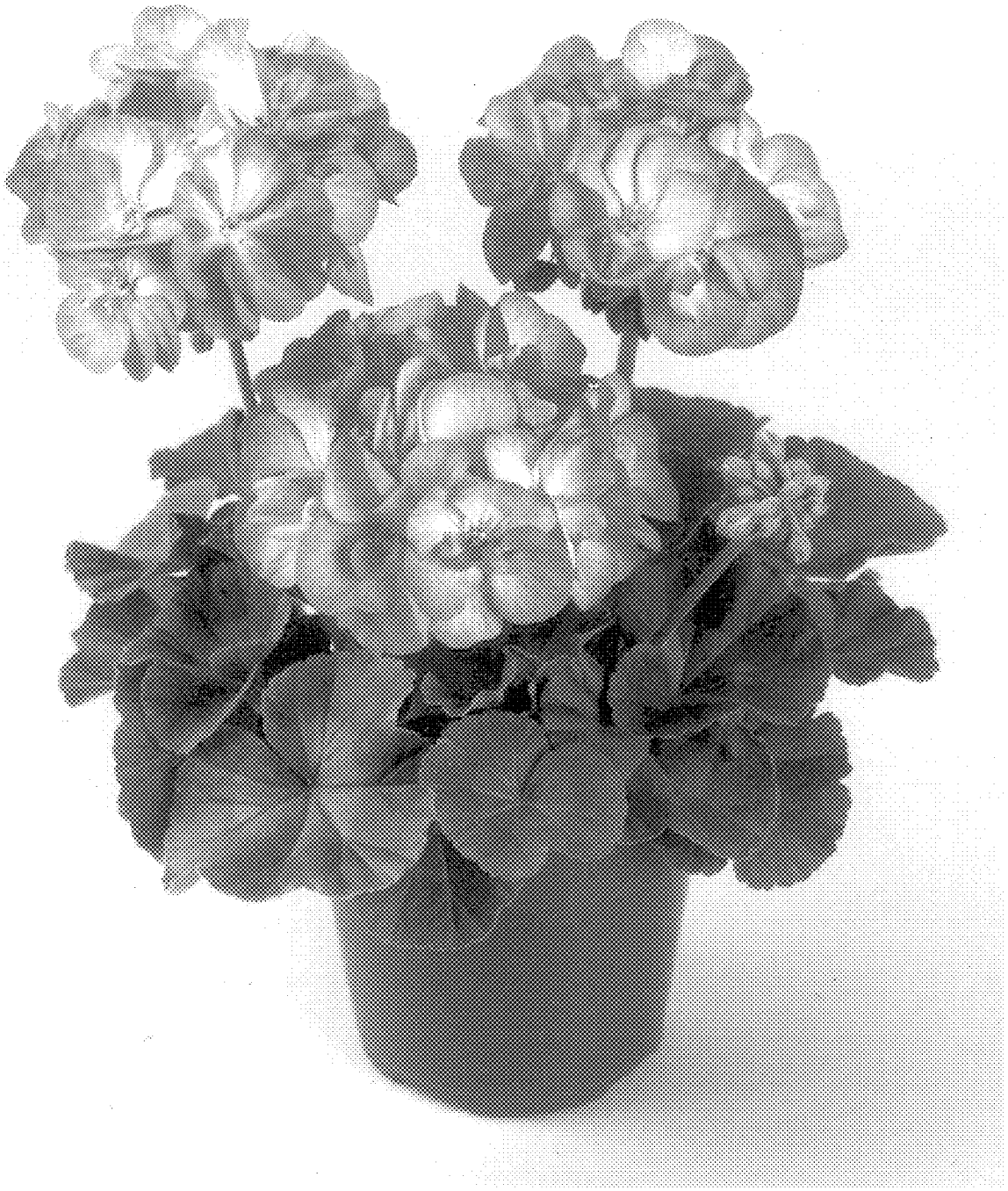

* * * * *